(12) United States Patent
L'alloret

(10) Patent No.: US 6,689,856 B2
(45) Date of Patent: Feb. 10, 2004

(54) WATER-SOLUBLE POLYMERS WITH A WATER-SOLUBLE BACKBONE AND SIDE UNITS WITH A LOWER CRITICAL SOLUTION TEMPERATURE, PROCESS FOR PREPARING THEM, AQUEOUS COMPOSITIONS CONTAINING THEM AND COSMETIC USE THEREOF

(75) Inventor: Florence L'alloret, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/145,142

(22) Filed: May 15, 2002

(65) Prior Publication Data

US 2002/0198328 A1 Dec. 26, 2002

(30) Foreign Application Priority Data

May 16, 2001 (FR) .............................................. 01 06450

(51) Int. Cl.$^7$ .............................................. C08F 116/12
(52) U.S. Cl. ....................... 526/333; 526/264; 526/265; 526/271; 526/274; 526/287; 526/288; 526/291; 526/303.1; 526/307.1; 526/307.5; 526/317.1; 526/330; 526/342
(58) Field of Search ................................. 526/264, 265, 526/271, 274, 287, 288, 291, 303.1, 307.1, 307.5, 317.1, 330, 333, 342

(56) References Cited

U.S. PATENT DOCUMENTS

| | | | |
|---|---|---|---|
| 5,939,485 A | 8/1999 | Bromberg et al. | |
| 6,018,033 A | 1/2000 | Chen et al. | |
| 6,171,610 B1 | * 1/2001 | Vacanti et al. | 424/426 |
| 6,296,831 B1 | * 10/2001 | Weller et al. | 424/1.29 |
| 6,316,011 B1 | * 11/2001 | Ron et al. | 424/401 |
| 6,486,213 B1 | * 11/2002 | Chen et al. | 514/772.1 |

FOREIGN PATENT DOCUMENTS

| | | |
|---|---|---|
| DE | 2 780 422 | 12/1999 |
| EP | 0 583 814 | 2/1994 |
| EP | 0 629 649 | 12/1994 |
| EP | 1 069 142 | 1/2001 |
| WO | WO 95/24430 | 9/1995 |
| WO | WO 97/00275 | 1/1997 |
| WO | WO 98/48768 | 11/1998 |
| WO | WO 00/35961 | 6/2000 |

OTHER PUBLICATIONS

M. Vamvakaki, et al., Polymer, vol. 40, No. 18, pp. 5161–5171, XP–004164984, "Synthesis of Water–Soluble Statistical Copolymers and Terpolymers Containing Pendent Oligo(Ethylene Glycol Derivatives)", Aug. 1999.

D. Hourdet, et al., Polymer, vol. 38, No. 10, pp. 2535–2547, XP–004059755, "Synthesis of Thermoassociative Copolymers", May 1, 1997.

D. Hourdet, et al., Polymer, vol. 35, No. 12, pp. 2624–2630, "Reversible Thermothickening of Aqueous Polymer Solutions", 1994.

F. L'Alloret, et al., Revue de L'Institut Francais de Petrole, vol. 52, No. 2, pp. 117–128, "Reversible Thermoassociation of Water–Soluble Polymers", 1997.

F. L'Alloret, et al., Coll. Polym. Sci., vol. 273, No. 12, pp. 1163–1173, "Aqueous Solution Behavior of New Thermoassociative Polymers", 1995.

L. D. Taylor, et al., Journal of Polymer Science, vol. 13, pp. 2551,2570, "Preparation of Films Exhibiting a Balanced Temperature Dependence to Permeation by Aqueous Solutions–A Study of Lower Consolute Behavior", 1975.

F. E. Bailey, Jr., et al., Journal of Applied Polymer Science, vol. 1, No. 1, pp. 56–62, "Some Properties of Poly(Ethylene Oxide)$^1$ in Aqueous Solution", 1959.

M. Heskins, et al., J. Macromol. Sci., A2, vol. 8, pp. 1441–1455, Solution Properties of Poly(N–Isopropylacrylamide), Dec. 1968.

* cited by examiner

*Primary Examiner*—Helen L. Pezzuto
(74) *Attorney, Agent, or Firm*—Oblon, Spivak, McClelland, Maier & Neustadt, P.C.

(57) ABSTRACT

Water-soluble polymers having a water-soluble backbone and side units having in water a lower critical solution temperature, LCST, the polymers being obtainable by free-radical precipitation polymerization of water-soluble monomers and of macromonomers comprising a unit with an LCST whose heat-induced demixing temperature in aqueous solution is from 5 to 40° C. for a concentration by mass in water of 1% of the said unit. Also described is a process for preparing these polymers by free-radical precipitation polymerization, and aqueous compositions containing these polymers and the use of these polymers and compositions, especially in cosmetics, for the cleansing and/or making up and/or care and/or antisun protection of keratin materials.

39 Claims, No Drawings

WATER-SOLUBLE POLYMERS WITH A WATER-SOLUBLE BACKBONE AND SIDE UNITS WITH A LOWER CRITICAL SOLUTION TEMPERATURE, PROCESS FOR PREPARING THEM, AQUEOUS COMPOSITIONS CONTAINING THEM AND COSMETIC USE THEREOF

BACKGROUND OF THE INVENTION

1. Field of the Invention

The invention relates to water-soluble polymers comprising a water-soluble backbone and side units with a lower critical solution temperature (LCST) having a specific precipitation temperature in water.

The invention also relates to the preparation process for the synthesis of these polymers.

Finally, the invention relates to aqueous compositions containing these polymers and to the use of these polymers and compositions, especially in cosmetics.

2. Discussion of the Background

The technical field of the invention may be defined as that of water-soluble polymers comprising a water-soluble backbone and side units with an LCST. It is known that these polymers have, in aqueous solution, gelling properties stimulated by an increase in the temperature.

This novel Theological behaviour is particularly advantageous in cosmetics and pharmaceuticals, since it makes it possible to obtain aqueous systems that are fluid at room temperature and gels at the temperature of the human body, that is to say fluid compositions (emulsions, dispersions, lotions, etc.) that gel when applied.

This type of application of the heat-induced gelling power is described in the case of aqueous solutions and emulsions in patents WO-95/24430 (University of Washington, Hoffman), U.S. Pat. No. 5,939,485 (Medlogic Global Corporation, Bromberg), WO-97/00275 (Gel Sciences, Inc, Bromberg) and WO-98/48768 (Medlogic Global Corporation, Bromberg).

Various synthetic processes have been used to obtain polymers of this novel type; these processes are as follows:

I) Reaction for grafting chains with an LCST onto water-soluble macromolecules, using a coupling agent such as dicyclohexylcarbodiimide or 1-(3-dimethylaminopropyl)-3-ethylcarbodiimide hydrochloride. The polymers obtained have a "comb" structure. This synthetic route is described by Hourdet (Hourdet D., L'Alloret F., Audebert R., Polymer, 1997, 38 (10), 2535–2547), in patents EP 583 814, EP 629 649 (Schlumberger Dowell, Maroy), WO-95/24430 (University of Washington, Hoffman).

This synthetic route is difficult to transfer to the industrial scale for reasons of cost (coupling agent and reaction in relatively dilute medium) and of toxicity (coupling agent).

II) Copolymerization of a macromonomer with an LCST and of a water-soluble monomer in homogeneous medium (water or organic solvent) or in emulsion.

This synthetic route in homogeneous medium is described by Hourdet (Hourdet D., L'Alloret F., Audebert R., Polymer, 1997, 38 (10), 2535–2547), in patents EP 583 814, EP 629 649 (Schlumberger Dowell, Maroy), WO-95/24430 (University of Washington, Hoffman). The reverse-emulsion polymerization process is described in patent WO-00/35961 (Rhodia, Yeung). The polymers obtained have a "comb" structure.

Industrially, the synthetic process in homogeneous medium requires the use of large amounts of water or of solvent, the content of active material in the reaction medium generally being less than 10%. The polymer is obtained either as an aqueous solution at a content of less than 10%, which limits its use in terms of formulation; or as an organic solvent and, in this case, must undergo a recovery phase, for example by precipitation.

For the emulsion polymerization, the contents of active materials are larger. However, the recovery of the polymer requires the introduction of large amounts of salt ($Na_2CO_3$ or NaOH) in order to obtain the polymer in solid form; or alternatively leads to an aqueous system containing, after inversion of the phases, the polymer and surfactants.

III) Coupling reaction between water-soluble blocks and blocks with an LCST.

This synthetic route, described in patent WO-95/24430 (University of Washington, Hoffman), leads to multiblock polymers. It requires the use of hydrophilic blocks and blocks with an LCST that are functionalized, thus inducing a multi-step process, namely synthesis of the two types of blocks, followed by a coupling reaction.

IV) Free-radical polymerization of water-soluble monomers in the presence of oxyalkylenated derivatives.

This synthetic route, performed in aqueous medium, for example in patents U.S. Pat. No. 5,939,485, WO-97/00275 and WO-98/48768 and in reverse emulsion in patent WO-00/35961, is based on reactions for transferring radicals to the oxyalkylenated chains and leads to compounds of complex structure whose properties in aqueous medium are difficult to control.

V) Free-radical polymerization of a macromonomer bearing chains of $C_m(OE)_n$ type and of a monomer bearing at least one unsaturated function.

Patent application EP-1 069 142 (Clariant) describes any water-soluble polymer obtained by free-radical polymerization of a hydrocarbon-based monomer that may contain oxygen, nitrogen, sulphur, phosphorus, chlorine and/or fluorine atoms, and of a macromonomer comprising an oxyalkylenated unit and a hydrophobic unit of $C_mH_{2m+1}$ type, in which m is an integer between 0 and 30. According to claim 4, the number m is preferably between 10 and 22. Claims 8 and 9 relate to polymers having in aqueous solution, above a critical temperature, a constant viscosity or else heat-induced thickening power. In this case, the macromonomers used contain a unit with an LCST in water.

When the number m is greater than 6, the grafts of these "comb" polymers are alkylethoxylated surfactants, these compounds being known to have in water a cloud point by raising the temperature. The corresponding grafted polymers are, below this cloud point, of associative nature since they bear hydrophobic alkyl units. They thus have gelling properties below the cloud point of their grafts (see comparative example 1, pages 14 and 15 of EP-A-1,069,142). Moreover, these polymers containing alkylethoxylated grafts are liable to interact with the surfactants present in the medium, and particularly with amphiphiles of the same chemical nature; this sensitivity to surfactants limits the flexibility of these systems in terms of formulation. It should moreover be noted that the heat-induced gelling properties given in the examples are observed above 90° C.

Example 17 describes a polymer bearing polyoxyethylenated grafts (m=0); however, its rheological behaviour in aqueous medium as a function of the temperature is not described.

Claim 11 specifies the preferred synthetic process, based on a free-radical polymerization by precipitation from tert-butanol.

SUMMARY OF THE INVENTION

In conclusion, this patent application describes a synthetic route that is simple to carry out industrially, using a non-toxic solvent that is suitable for cosmetic applications and for which the polymer/solvent ratio is greater than in the case of processes performed in homogeneous medium. The heat-induced gelling polymers described in this patent application bear heat-sensitive chains containing oxyalkylenated units; however, all the polymers described have a gelpoint of greater than 90° C., which is relatively unsuitable for cosmetic applications.

There is thus a need for water-soluble polymers comprising a water-soluble backbone bearing units with an LCST, which, inter alia:

are suitable for cosmetic uses, with a precipitation temperature of the units at 1% in water that is in a cosmetically advantageous range;

whose synthetic process can be extrapolated to the industrial scale while at the same time allowing good control of the structure of the macromolecules, and thus of their properties in solution and in film form.

The present invention satisfies these needs.

This aim and others are achieved, in accordance with the invention, by means of a water-soluble polymer comprising a water-soluble backbone and side units having in water a lower critical solution temperature, LCST, the polymer being able to be obtained by free-radical precipitation polymerization of:

a) one or more water-soluble monomers (Ia) and, optionally, of one or more hydrophobic monomers (Ib) in a small amount relative to the monomers (Ia), the said monomers (Ia) and (Ib) bearing at least one unsaturated function that can be polymerized to form the water-soluble backbone;

b) one or more macromonomers corresponding to formula (II) below:

A—X—B (II), in which A is a group comprising at least one unsaturated hydrocarbon-based bond that may be polymerized; X is a group chosen from —O—, —S—, —PH—, —NH— and NR° in which R° is an alkyl group of 1 to 6 carbon atoms; and B is a unit with an LCST whose heat-induced demixing temperature in aqueous solution is from 5 to 40° C. for a concentration by weight in water of 1% of the said unit.

In the water-soluble backbone, the water-soluble monomer(s) (Ia) is(are) in an amount that is sufficient to allow the water-solubility of the water-soluble backbone. The expression "water-soluble backbone" means a backbone that is soluble in water at 5° C. to 80° C., to a proportion of at least 10 g/l and preferably at least 20 g/l.

Surprisingly, the polymers according to the invention, which are water-soluble polymers bearing specific units with an LCST, are entirely suitable, in particular for cosmetic use, due to the specific precipitation temperature of the units with an LCST at 1% in water, which is in the range from 5 to 40° C.

These polymers, in particular due to the way in which they are prepared, have a fully controlled, regulated and fully defined structure.

Consequently, their properties, for example in solution form and in film form, are also fully defined and controlled.

The invention also relates to a process for preparing the polymer, as has been described above, in which:

the free-radical precipitation copolymerization of one or more water-soluble monomers (Ia), possibly of one or more water-soluble monomers (Ib) in a small amount relative to the monomers (Ia), and of one or more macromonomers of formula (II) is performed in a medium comprising an alcohol and water;

the polymer obtained is isolated.

This process allows the preparation of the polymers described above, simply and quickly, by a reliable and proven free-radical precipitation polymerization in an aqueous-alcoholic medium.

This process comprises few steps, and in fact essentially only one step, and is thus quick and inexpensive.

The alcohol of this medium is preferably tert-butanol. This synthetic process has the advantages, inter alia, of being carried out in cosmetically acceptable media, of being easy to extrapolate to the industrial scale, and of allowing full control of the structure of the polymers or macromolecules obtained, and thus of their properties in solution form and in film form.

It should be noted that a process of free-radical precipitation polymerization, especially in tert-butanol, is known from document EP-A-1 069 142, but it was not absolutely obvious to transfer such a process, so as to prepare the specific polymers according to the invention, whose structure is fundamentally different from that of the polymers in document EP-A-1 069 142.

Specifically, in particular, the macromonomers forming part of the composition of the polymer according to the invention comprise units with an LCST whose specific LCST temperature is markedly lower, namely by 5 to 40° C. at 1% in water, than that of the polymers of document EP-A-1 069 142.

The polymer according to the invention is a polymer comprising a water-soluble backbone and units having in water a lower critical solution temperature (LCST), also known as "units with an LCST".

In this respect, it is useful to recall that the expression "units with an LCST" means units whose solubility in water is modified beyond a certain temperature. These are units with a heat-induced demixing temperature (or cloud point) defining their region of solubility in water. The minimum demixing temperature obtained as a function of the concentration of polymer consisting solely of units with an LCST is known as the "LCST" (Lower Critical Solution Temperature). For each concentration of LCST polymer, a heat-induced demixing temperature is observed. It is higher than the LCST, which is the minimum point of the curve. Below this temperature, the polymer is soluble in water, and above this temperature, the polymer loses its solubility in water.

The units with an LCST of the polymer have, according to the invention, a heat-induced demixing temperature of from 5 to 40° C. for a concentration by mass in water of 1% by weight of the said units with an LCST.

Preferably, the heat-induced demixing temperature in aqueous solution of the units with an LCST of the polymer is from 10 to 35° C., more preferably from 10 to 30° C., including all values and sub-ranges therebetween, for a concentration by weight in water of 1% of the units with an LCST.

The polymer according to the invention having the structure described above with water-soluble units and specific units with an LCST defined above has in aqueous solution gelation properties beyond a critical temperature, or heat-gelling properties.

These heat-gelling properties observed beyond the demixing temperature of the LCST chains are described in the prior art, especially in documents D. Hourdet et al., Polymer 1994, Vol. 35, No. 12, pages 2624–2630, F. L'Alloret et al., Coll. Polym. Sci., 1995, Vol. 273, No. 12, pages 1163–1173, and F. L'Alloret, Revue de l'Institut Français du Pétrole [Review of the French Petroleum Institute], 1997, Vol. 52, No. 2, pages 117–128. They are due to the combination of the LCST chains within hydrophobic microdomains beyond their demixing temperature, thus forming crosslinking nodes between the main chains.

These gelling properties are observed when the polymer concentration is sufficient to allow interactions between LCST grafts borne by different macromolecules. The minimum concentration required, known as the "critical aggregation concentration", or CAC, is evaluated by rheological measurements: it is the concentration at and above which the viscosity of an aqueous solution of the polymers of the invention becomes higher than the viscosity of a solution of the equivalent polymer not comprising LCST chains.

Beyond the CAC, the polymers of the invention have gelling properties when the temperature becomes higher than a critical value, known as the "gel point", or $T_{gel}$. According to the literature data, there is good agreement between $T_{gel}$ and the demixing temperature of the LCST chains, under the same concentration conditions. The gel point of an aqueous solution of a polymer of the invention is determined by rheological measurements: it is the temperature at and above which the viscosity of a solution of a polymer of the invention becomes higher than the viscosity of a solution of the equivalent polymer not comprising LCST chains.

The polymers of the invention are characterized by a specific gel point generally of from 5 to 40° C., preferably from 10 to 35° C., for a concentration by mass in water equal to, for example, 2% by weight.

This specific gel point allows these polymers to give the compositions into which they are incorporated a number of properties, and in particular a wide variety of forms at room temperature, and a gelled foam texture effect when applied.

Polymers comprising, in the manner of those used in the compositions of the invention, water-soluble units and units with an LCST and having heat-induced gelling properties observed above the demixing temperature of the LCST chains are described in the documents already mentioned above.

Document D. Hourdet et al., Polymer, 1994, Vol. 35, No. 12, pages 2624–2630 relates to the reversible heat-induced thickening of aqueous solutions of copolymers comprising a water-soluble backbone of polyacrylic acid with poly (ethylene oxide) (PEO) grafts.

Document F. L'Alloret et al., Coll. Polym. Sci., 1995, Vol. 273, No. 12, pages 1163–1173 relates to the heat-induced thickening behaviour in aqueous solution of polymers comprising a 2-acrylamido-2-methylpropanesulphonic acid (AMPS) backbone and poly(ethylene oxide) side chains.

Similarly, document F. L'Alloret, Revue de l'Institut Français du Pétrole [Review of the French Petroleum Institute], 1997, Vol. 52, No. 2, pages 117–128 describes the reversible heat-induced association of copolymers with a polyacrylic water-soluble backbone or based on AMPS with PEO grafts.

Polymers, such as those mentioned in these three documents, find their use in particular in the petroleum industry.

Thus, document EP-A-0 583 814 describes thermoviscosifying polymers with a water-soluble backbone comprising segments with an LCST, or bearing side chains with an LCST, which may be used especially as thickeners, constituents of drilling fluids or other fluids, and industrial cleaning fluids.

Document EP-A-0 629 649 describes polymers similar to those of document EP-A-0 583 814 and their use as anti-sedimentation agents for suspensions, possibly in cosmetic preparations.

It should be noted that none of the documents referred to above describes polymers presenting the specific structure of polymers according to the invention.

Document WO-A-95 24430 also describes copolymers comprising a backbone consisting of pH-sensitive units, for example polyacrylic units, and heat-sensitive units, grafted onto this backbone. These copolymers have heat-induced gelling properties and they are used for the liberation and controlled release of active principles or pharmaceutical agents, and possibly cosmetic agents, by topical application.

The polymers according to document WO-A-95 24430 are characterized by the extremely inconvenient opacity of the heat-induced products, which is not the case for the polymers of the invention.

In point of fact, the polymer in the said document is fundamentally different from that of the invention since it has overall for the entire polymer an LCST in the temperature range from 20 to 40° C., in contrast with the polymers of the invention, which are water-soluble for any temperature between 5° C. and 80° C.

Documents U.S. Pat. No. 5,939,485 and WO-A-97 00275 describe reversible-gelling polymer systems, comprising a sensitive component capable of aggregation, in response to a change in an external "stimulus", and a structural component. The external stimulus may be, for example, the temperature.

The component that is sensitive to the external stimulus is fundamentally different from the units with an LCST of the application. Specifically, these components that are sensitive to the external stimulus in fact consist of at least one hydrophilic fragment and one hydrophobic fragment. Thus, the sensitive component may be a block copolymer, such as a "poloxamer", for example a Pluronic®, which is a block polymer of ethylene oxide (soluble) and of propylene oxide (insoluble); such a block copolymer aggregates microscopically beyond a critical temperature not corresponding to an LCST. A nonionic surfactant may also be used as sensitive component.

Document U.S. Pat. No. 5,939,485 relates more particularly to a polymer network formed from a water-soluble polyacrylic backbone and a Pluronic® sensitive component, which is interlocked in the said backbone, without covalent bonding; this network thus has a particular structure that has nothing in common with the polymer of the invention. On the other hand, in document WO-A-97 00275, it is a matter of polymers with covalent bonds.

These polymers have heat-induced gelling properties and they may be used in the pharmaceutical field for the delivery of medicinal products and in many other fields, including the cosmetics field.

In these formulations, the sensitive component of the polymer system has a behaviour that is different from that of the units with an LCST, such as those of the polymer of the invention, during heating. Thus, when the said sensitive component (for example poloxamer) is heated to about 30–40° C., it shows a temperature of micellization, that is to say an aggregation at the microscopic level, and then, when it is heated further, an LCST temperature that is very much higher. This LCST corresponds to an aggregation at the macroscopic level between the macromolecules. It is explained in WO-A-97/00275 on pages 16 and 17 that the gelation and the LCST are observed at temperatures which differ by about 70° C., the gel point corresponding to the micellization temperature of the sensitive component, which shows that these polymers are different from those of our application. In addition, it is not possible, on account of the synthesis used in WO-A-97/00275, to fully control the structure and properties of the final polymer obtained, as is the case in the compositions of the invention. Specifically, the preparation of the polymers of the invention, by free-radical polymerization of specific macromonomers containing units with an LCST and of monomers, makes it possible, on the contrary, to fully regulate and control the structure and properties of the polymer.

Cosmetic compositions using a reversible heat-induced gelling polymer system, comprising polyacrylic acid and a poloxamer as in documents U.S. Pat. No. 5,939,485 and WO-A-97/00275, are also known from document WO-A-98/48768. Once again, the polymer system of these documents is fundamentally different from those used in the compositions of the invention, to the point that the advantageous properties of the polymers of the invention cannot be obtained.

WO-A-00/35961 describes the preparation of polymers with heat-induced thickening properties by emulsion polymerization and the use of these polymers in pharmaceutical and cosmetic compositions. These polymers may be copolymers containing water-soluble units and units with an LCST based on alkylene oxide. In this case also, the structure and process for preparing these polymers are fundamentally different from those of the invention.

It emerges from the text hereinabove that the structure of the polymers according to the invention containing, in particular, specific units with an LCST, and also the process for preparing them by free-radical precipitation polymerization in an aqueous-alcoholic medium, are neither described nor suggested in the documents of the prior art.

As has been mentioned above, the polymer according to the invention comprises a water-soluble backbone and units having in water an LCST, the said polymer being able to be obtained by free-radical polymerization of one or more water-soluble monomers (Ia), possibly of one or more hydrophobic monomers (Ib) in a smaller amount relative to the said monomers (Ia), the said monomers (Ia) and (Ib) forming the water-soluble backbone, and of one or more macromonomers (II) comprising units with an LCST.

The polymers of the invention are thus essentially generally grafted polymers whose backbone is water-soluble, the said backbone bearing grafts comprising units with an LCST.

The water-soluble backbone does not have a heat-induced demixing temperature.

The said polymers may be partially or totally crosslinked.

The water-soluble backbone predominantly comprises water-soluble units, these water-soluble units (Ia) being derived from monomers (Ia) bearing, before the polymerization, at least one unsaturated function.

The expression "water-soluble units" generally means that these units are soluble in water, at a temperature of from 5 to 80° C., to a proportion of at least 10 g/l and preferably of at least 20 g/l.

The water-soluble backbone may also optionally comprise one or more hydrophobic monomer units derived from the monomers (Ib), the said hydrophobic units being optionally present, but in a small amount, for example less than 20%, that is to say in an amount that is low enough for the water-soluble backbone of the polymer to be soluble in water.

The water-soluble backbone does not have a heat-induced demixing temperature of LCST type.

By way of example, the water-soluble monomer(s) (Ia) can be chosen from the following monomers or salts thereof:

(meth)acrylic acid;

acrylamido-2-methylpropanesulphonic acid (AMPS);

styrenesulphonic acid;

vinylsulphonic acid;

(meth)allylsulphonic acid;

(meth)acrylamide;

vinylphosphonic acid;

N-vinylacetamide;

N-methyl-N-vinylacetamide;

N-vinylformamide;

N-methyl-N-vinylformamide;

N-vinyllactams comprising a cyclic alkyl group of 4 to 9 carbon atoms, such as N-vinylpyrrolidone, N-butyrolactam or N-vinylcaprolactam;

maleic anhydride;

itaconic acid;

vinyl alcohol of formula $CH_2=CHOH$;

dimethyldiallylammonium chloride;

quaternized dimethylaminoethyl methacrylate (DMAEMA);

(meth)acrylamidopropyltrimethylammonium chloride (APTAC and MAPTAC);

methylvinylimidazolium chloride;

2-vinylpyridine;

4-vinylpyridine;

glycidyl (meth)acrylate;

vinyl monomers of formula (III) below:

(III)

in which:
R is chosen from H, —$CH_3$, —$C_2H_5$ or —$C_3H_7$, and
X is chosen from:
alkyl oxides of —OR' type in which R' is a linear or branched, saturated or unsaturated hydrocarbon-based radical containing from 1 to 6 carbon atoms, optionally substituted with at least one halogen atom (iodine, bromine, chlorine or fluorine); a sulphonic (—$SO_3^-$), sulphate (—$SO_4^-$); phosphate (—$PO_4H_2$); hydroxyl (—OH); primary amine (—$NH_2$); secondary amine (—$NHR_1$), tertiary amine (—$NR_1R_2$) or quaternary amine (—$N^+R_1R_2R_3$) group with $R_1$, $R_2$ and $R_3$ being, independently of each other, a linear or branched, saturated or unsaturated hydrocarbon-based radical containing 1 to 6 carbon atoms, with the proviso that the sum of the carbon atoms of $R'+R_1+R_2+R_3$ does not exceed 6; and
—$NH_2$, —$NHR_4$ and —$NR_4R_5$ groups in which $R_4$ and $R_5$ are, independently of each other, linear or branched, saturated or unsaturated hydrocarbon-based radicals containing 1 to 6 carbon atoms, with the proviso that the total number of carbon atoms of $R_4+R_5$ does not exceed 6, the said $R_4$ and $R_5$ optionally being substituted with a halogen atom (iodine, bromine, chlorine or fluorine); a hydroxyl (—OH); sulphonic (—SO$_3^-$); sulphate (—SO$_4^-$); phosphate (—PO$_4$H$_2$); primary amine (—NH$_2$); secondary amine (—NHR$_1$), tertiary amine (—NR$_1$R$_2$) and/or quaternary amine (—N$^+$R$_1$R$_2$R$_3$) group with R$_1$, R$_2$ and R$_3$ being, independently of each other, a linear or branched, saturated or unsaturated hydrocarbon-based radical containing 1 to 6 carbon atoms, with the proviso that the sum of the carbon atoms of R$_4$+R$_5$+R$_1$+R$_2$+R$_3$ does not exceed 6; such as N,N-dimethylacrylamide and N,N-diethylacrylamide.

The hydrophobic monomer(s) (Ib), which may be present in small amounts to form the backbone, may be chosen for example from the following monomers or salts thereof:

vinylacetate of formula CH$_2$=CH—OCOCH$_3$;
acrylonitrile;
vinyl chloride;
vinylidene chloride;
vinyl monomers of formula (III) below:

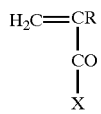

(III)

in which:
R is chosen from H, —CH$_3$, —C$_2$H$_5$ or —C$_3$H$_7$, and X is chosen from:
alkyl oxides of —OR' type in which R' is a linear or branched, saturated or unsaturated hydrocarbon-based radical containing from 7 to 22 carbon atoms, optionally substituted with at least one halogen atom (iodine, bromine, chlorine or fluorine); a sulphonic (—SO$_3^-$), sulphate (—SO$_4^-$), phosphate (—PO$_4$H$_2$); hydroxyl (—OH); primary amine (—NH$_2$); secondary amine (—NHR$_1$), tertiary amine (—NR$_1$R$_2$) or quaternary amine (-N$^+$R$_1$R$_2$R$_3$) group with R$_1$, R$_2$ and R$_3$ being, independently of each other, a linear or branched, saturated or unsaturated hydrocarbon-based radical containing from 7 to 22 carbon atoms, with the proviso that the sum of the carbon atoms of R'+R$_1$+R$_2$+R$_3$ does not exceed 22; and —NH$_2$, —NHR$_4$ and —NR$_4$R$_5$ groups in which R$_4$ and R$_5$ are, independently of each other, linear or branched, saturated or unsaturated hydrocarbon-based radicals containing 7 to 22 carbon atoms, with the proviso that the total number of carbon atoms of R$_4$+R$_5$ does not exceed 22, the said R$_4$ and R$_5$ optionally being substituted with a halogen atom (iodine, bromine, chlorine or fluorine); a hydroxyl (—OH); sulphonic (—SO$_3^-$); sulphate (—SO$_4^-$); phosphate (—PO$_4$H$_2$); primary amine (—NH$_2$); secondary amine (—NHR$_1$), tertiary amine (—NR$_1$R$_2$) and/or quaternary amine (—N$^+$R$_1$R$_2$R$_3$) group with R$_1$, R$_2$ and R$_3$ being, independently of each other, a linear or branched, saturated or unsaturated hydrocarbon-based radical containing 7 to 22 carbon atoms, with the proviso that the sum of the carbon atoms of R$_4$+R$_5$+R$_1$+R$_2$+R$_3$ does not exceed 22; such as N,N-dimethylacrylamide and N,N-diethylacrylamide.

These optional hydrophobic monomers (Ib) are generally present in an amount that is low enough for the water-soluble backbone of the polymer to be, specifically, soluble in water.

The water-soluble backbones are preferably totally or partially neutralized with a mineral or organic base.

This base may be chosen, for example, from sodium, ammonium, lithium, calcium and magnesium salts, salts of ammonium substituted with 1 to 4 alkyl groups containing from 1 to 15 carbon atoms, or alternatively from monoethanolamine, diethanolamine, triethanolamine, aminomethylpropanediol, N-methylglucamine and basic amino acids, such as arginine and lysine, and mixtures thereof.

The polymer, and in particular the water-soluble backbone, may be totally or partially crosslinked, using, for example, the crosslinking agents or compounds containing olefinic polyunsaturation commonly used for the crosslinking of polymers obtained by free-radical polymerization. Examples of these crosslinking agents that may be mentioned include divinylbenzene, diallyl ether, triallylamine, tetraallylethylenediamine, dipropylene glycol diallyl ether, polyglycol diallyl ethers, hydroquinone diallyl ether, trimethylolpropane diallyl ether, tetraallyloxyethane, allylic ethers of alcohols of the sugar series, polyallyl esters, tetraallyloxyethanoyl or other polyfunctional alcohol allyl or vinyl ethers, triethylene glycol divinyl ether, allylic esters of vinylphosphonic acid and of phosphoric acid, compounds comprising two or three (meth)acrylate or (meth)acrylamide groups, such as ethylene glycol diacrylate, tetraethylene glycol diacrylate, butanediol diacrylate, allyl methacrylate, trimethylolpropane triacrylate (TMPTA) and methylenebisacrylamide, or mixtures thereof.

Methylenebisacrylamide, allyl methacrylate or trimethylolpropane triacrylate (TMPTA) will be used more particularly.

The degree of crosslinking will preferably range from 0.01 mol % to 10 mol % and more particularly from 0.2 mol % to 7 mol % relative to the polymer.

The crosslinking of the polymer, and in particular of the water-soluble skeleton, may also be carried out using a multifunctional macromonomer with an LCST (II), for example bearing two or three unsaturated functions, which is introduced into the reaction medium during the polymerization (in addition to the components a) and b)), in suitable proportions, so as to obtain a molar degree of crosslinking of from 0.01 to 10%.

Preferably, the water-soluble backbone has a molar mass ranging from 1 000 g/mol to 50 000 000 g/mol and preferably from 10 000 g/mol to 10 000 000 g/mol.

According to the invention, the polymer is obtained by free-radical polymerization of the monomers (Ia) and, optionally, (Ib) described above and of one or more macromonomers corresponding to formula (II) already given above.

In formula (II), X is a divalent group chosen, for example, from —O—, —S—, —PH—, —NH— and —NR°—, in which R° is an alkyl group of 1 to 6 carbon atoms.

A is a group comprising at least one unsaturated hydrocarbon-based bond that may be polymerized (via a free-radical route).

The group A may be chosen, for example, from vinyl, allyl, acryl and methacryl groups.

The macromonomer (II) also, fundamentally, comprises units B with an LCST.

The units with an LCST of the polymers used in the invention may be defined as being units whose water solubility is modified beyond a certain temperature. They are units with a heat-induced demixing temperature (or cloud point) defining their region of solubility in water. The minimum demixing temperature obtained as a function of the polymer concentration is referred to as the "LCST" (Lower Critical Solution Temperature). For each polymer concentration, a heat-induced demixing temperature is observed; it is higher than the LCST, which is the minimum point of the curve. Below this temperature, the polymer constituting the unit with an LCST is soluble in water; above this temperature, the polymer constituting the unit with an LCST loses its solubility in water.

Some of these polymers with an LCST are especially described in the articles by Taylor et al., Journal of Polymer Science, part A: Polymer Chemistry, 1975, 13, 2 551; by J. Bailey et al., Journal of Applied Polymer Science, 1959, 1,56; and by Heskins et al., Journal of Macromolecular Science, Chemistry A2, 1968, vol. 8, 1 441.

The expression "soluble in water at a temperature T" means that the units have a solubility at T of at least 1 g/l and preferably of at least 2 g/l.

The measurement of the LCST may be performed visually: the temperature at which the cloud point of the aqueous solution appears is determined; this cloud point is reflected by the opacification of the solution, or loss of transparency.

In general, a transparent composition will have a maximum light transmittance value, irrespective of the wavelength of between 400 and 800 nm, through a sample 1 cm thick, of at least 85% and preferably of at least 90%.

The transmittance may be measured by placing a sample 1 cm thick in the light beam of a spectrophotometer working in the wavelengths of the light spectrum.

The units with an LCST of the polymers used in the invention may consist of one or more polymers chosen from the following polymers:

polyethers such as polyethylene oxide (PEO), polypropylene oxide (PPO) or random copolymers of ethylene oxide (EO) and of propylene oxide (PO), polyvinyl methyl ethers, polymeric and copolymeric N-substituted acrylamide derivatives with an LCST, such as poly-N-isopropylacrylamide (Nipam) and poly-N-ethylacrylamide, and poly-N-vinylcaprolactam and N-vinylcaprolactam copolymers.

Preferably, the units with an LCST consist of polypropylene oxide $(PPO)_n$ with n being an integer from 10 to 50, or of random copolymers of ethylene oxide (EO) and of propylene oxide (PO), represented by the formula $(EO)_m (PO)_n$ in which m is an integer ranging from 1 to 40, preferably from 2 to 20, more preferably from 2 to 10, including all values and subranges therebetween, and n is an integer ranging from 10 to 60 and preferably from 20 to 50.

Preferably, the molar mass of these units with an LCST is from 500 to 5300 g/mol more preferably from 1000 to 4000 g/mol, most preferably from 1500 to 3000 g/mol, including all values and subranges therebetween.

It has been found that the random distribution of the EO and PO units is reflected by the existence of a lower critical solution temperature, beyond which a macroscopic phase separation is observed. This behaviour is different from that of the block (EO) (PO) copolymers, which form micelles beyond a critical temperature known as the micellization temperature (microscopic level aggregation).

The units with an LCST may thus especially be amino, especially monoamino, diamino or triamino, random copolymers of ethylene oxide and of propylene oxide.

Among these commercially available polymers with an LCST that may be mentioned are the copolymers sold under the name Jeffamine® by Huntsman, and especially Jeffamine® XTJ-507 (M-2005), Jeffamine® B-2000 and Jeffamine® XTJ-509 (or T-3000).

The units with an LCST may also be derived from random EO/PO copolymers containing OH end groups, such as those sold under the name Polyglycols® P41 and B11 by Clariant.

Polymeric and copolymeric N-substituted acrylamide derivatives having an LCST, and also poly-N-vinylcaprolactam and N-vinyl caprolactam copolymers may also be used in the invention as units with an LCST.

As examples of polymeric and copolymeric N-substituted acrylamide derivatives having an LCST, mention may be made of poly-N-isopropylacrylamide, poly-N-ethylacrylamide and copolymers of N-isopropylacrylamide (or of N-ethylacrylamide) and of one or more monomers chosen from the monomers (Ia) and (Ib).

The molar mass of these polymers is preferably from 1000 g/mol to 30 000 g/mol.

These polymers may be synthesized by free-radical polymerization using a pair of initiators such as aminoethanethiol hydrochloride, in the presence of potassium persulphate, so as to obtain precursor oligomers with a reactive amino end group.

As examples of N-vinylcaprolactam copolymers, mention may be made of copolymers of N-vinylcaprolactam and of one or more monomer(s) chosen from the vinyl monomers (Ia) and (Ib) defined above.

The molar mass of these N-vinylcaprolactam polymers or copolymers is generally from 1000 g/mol to 30 000 g/mol.

These compounds may be synthesized by free-radical polymerization using a pair of initiators such as aminoethanethiol hydrochloride, in the presence of potassium persulphate, so as to obtain units with an LCST having a reactive amino end group.

The proportion by mass of units with an LCST in the final polymer is preferably from 5% to 70%, especially from 20% to 65% and particularly from 30% to 60% by weight relative to the final polymer.

As seen above, the heat-induced demixing temperature of the said units with an LCST of the polymer used in the invention is from 5 to 40° C. and preferably from 10 to 35° C., for a concentration by mass in water of 1% by weight of the said units with an LCST.

A macromonomer (II) with an LCST is obtained by reaction between a unit with an LCST bearing at least one reactive site and a compound comprising at least one additional reactive site and at least one unsaturated hydrocarbon-based bond such as a vinyl or allyl function; examples that are mentioned include (meth)acrylic acid, maleic anhydride, itaconic acid, vinyl alcohol, vinyl acetate, glycidyl (meth)acrylate, 3-chloropropene, 4-isocyanatostyrene and chloromethylsytrene. A reactive site may be chosen especially from alcohol, glyceryl ester, isocyanate, primary, secondary or tertiary amine, carboxylic acid and halogen functions. A reactive site of the carboxylic acid or ester type will, especially, generally react with a reactive site of the alcohol or amine type; an isocyanate site will rather react with an alcohol site, and a halogen site will rather react with an alcohol or amine site. The reactions used may be, for example, an esterification, a transesterification, an amidation or a nucleophilic substitution.

According to the invention, the polymers described above are prepared by carrying out the free-radical precipitation copolymerization of one or more water-soluble monomers (Ia) already defined above, optionally of one or more hydrophobic monomers (Ib) already defined above, in a small amount relative to the said water-soluble monomers (Ia), and of one or more macromonomers of formula (II) already described above, in a medium comprising an alcohol and water (aqueous-alcoholic medium), and by isolating the polymer obtained.

The alcohol used is water-miscible and is generally an aliphatic alcohol containing from 1 to 4 carbon atoms, such as, for example, methanol, ethanol, propanol, isopropanol and, preferably, tert-butanol. The mass content of water is generally less than or equal to 10% and preferably less than 5% by weight.

According to one advantageous characteristic of the process, such alcohols are entirely cosmetically compatible.

The monomers and macromonomers are totally or partially dissolved in the polymerization medium, whereas the polymer is insoluble therein.

The polymerization reaction is carried out at a temperature of between −10° C. and 100° C. and preferably between 20° C. and 70° C.

The copolymerization is conventionally performed in the presence of a polymerization initiator.

Polymerization initiators are compounds that generate free radicals. These initiators may be chosen, for example, from aqueous hydrogen peroxide solution; organic peroxidized compounds such as benzoylperoxide, tert-butyl hydroperoxide, methyl ethyl ketone hydroperoxide; diazo compounds such as azobisisobutyronitrile or azobisdimethylvaleronitrile; oxidizing agent/reducing agent couples such as ammonium peroxydisulphate/sodium metabisulphite, and ammonium peroxydisulphate/N,N,N',N'-tetramethylenediamine.

The polymerization reaction may also be initiated using photoinitiators or by a radiation such as Uv, neutrons or by plasma.

The polymerization is carried out in an inert medium, preferably under a nitrogen or argon atmosphere.

The polymer appears in the reaction medium in the form of a white precipitate. It may be readily isolated using the usual separation, evaporation and drying processes. For example, the tert-butanol may be removed by filtration or distillation.

The polymers obtained satisfy the application properties described in patent applications FR-01 00485, FR-01 00480, FR-01 00478, FR-01 00481, FR-01 00483 and FR-01 05112.

The invention also relates to an aqueous composition comprising at least one polymer as defined above, and an aqueous phase.

The polymer(s) according to the invention is(are) preferably present in the aqueous compositions in an amount preferably of between 0.01% and 20% by weight, especially from 0.05% to 15% by weight and in particular from 0.1% to 10% by weight.

These compositions and the polymers they comprise find a most particular application in cosmetics and dermatology.

The said composition comprises, in addition to the polymer as defined above, an aqueous phase, which may comprise, in addition to water, a floral water such as cornflower water, a mineral water such as eau de Vittel, eau de Lucas or eau de La Roche Posay and/or a spring water.

It is possible to add to the said aqueous composition the constituents usually used in the envisaged type of application. Needless to say, a person skilled in the art will take care to select these optional additional constituents, and/or the amount thereof, such that the advantageous properties of the composition according to the invention are not, or are not substantially, adversely affected by the envisaged addition.

The said aqueous composition can form all or part of a cosmetic or dermatological composition that may thus moreover comprise a cosmetically or dermatologically acceptable medium, that is to say a medium that is compatible with an application to keratin materials such as the skin, the nails, the hair, the eyelashes and the eyebrows, mucous membranes and semi-mucous membranes, and any other area of body or facial skin.

The composition of the invention may be in any presentation form usually used in cosmetics and dermatology. It may be, for example, in the form of gels, in the form of oil-in-water (O/W) or water-in-oil (W/O) emulsions or multiple emulsions. The term "emulsion" means herein both dispersions without emulsifiers and dispersions comprising emulsifiers, or alternatively dispersions stabilized with solid particles or with lipid spherules of ionic or nonionic type.

In the compositions of the invention in emulsion form, the aqueous phase of the composition may be present in a concentration ranging, for example, from 5% to 80% and preferably from 30% to 70% by weight relative to the total weight of the composition, and the oily phase may be present in a concentration ranging from 5 to 70% and preferably from 10% to 50% by weight relative to the total weight of the composition.

The fatty phase or oily phase usually contains at least one oil. As oils that may be used in the composition of the invention, mention may be made, for example, of:

hydrocarbon-based oils of animal origin, such as perhydrosqualene;

hydrocarbon-based oils of plant origin, such as liquid triglycerides of fatty acids containing from 4 to 10 carbon atoms, for instance heptanoic or octanoic acid triglycerides or alternatively, for example, sunflower oil, corn oil, soybean oil, marrow oil, grapeseed oil, sesame oil, hazelnut oil, apricot oil, macadamia oil, arara oil, sunflower oil, castor oil, avocado oil, caprylic/capric acid triglycerides, for instance those sold by the company Stearineries Dubois or those sold under the names Miglyol 810, 812 and 818 by the company Dynamit Nobel, jojoba oil or karite butter oil;

synthetic esters and synthetic ethers, especially of fatty acids, for instance oils of formulae $R^1COOR^2$ and $R^1OR^2$ in which $R^1$ represents a fatty acid residue containing from 8 to 29 carbon atoms and $R^2$ represents a branched or unbranched hydrocarbon-based chain containing from 3 to 30 carbon atoms, such as, for example, purcellin oil, isononyl isononanoate, isopropyl myristate, 2-ethylhexyl palmitate, 2-octyldodecyl stearate, 2-octyldodecyl erucate or isostearyl isostearate; hydroxylated esters such as isostearyl lactate, octyl hydroxystearate, octyldodecyl hydroxystearate, diisostearyl malate, triisocetyl citrate and fatty alkyl heptanoates, octanoates and decanoates; polyol esters, for instance propylene glycol dioctanoate, neopentyl glycol diheptanoate and diethylene glycol diisononanoate; and pentaerythritol esters, for instance pentaerythrityl tetraisostearate;

linear or branched hydrocarbons of mineral or synthetic origin, such as volatile or non-volatile liquid paraffins, and derivatives thereof, petroleum jelly, polydecenes, and hydrogenated polyisobutene such as Parleam® oil;

fatty alcohols containing from 8 to 26 carbon atoms, for instance cetyl alcohol, stearyl alcohol and a mixture thereof (cetylstearyl alcohol), octyldodecanol, 2-butyloctanol, 2-hexyldecanol, 2-undecylpentadecanol, oleyl alcohol or linoleyl alcohol;

alkoylated and especially ethoxylated fatty alcohols such as oleth-12;

partially hydrocarbon-based and/or silicone-based fluoro oils, for instance those described in document JP-A-2 295 912. Examples of fluoro oils which may also be mentioned include perfluoromethylcyclopentane and perfluoro-1,3-dimethylcyclohexane, sold under the names "Flutec PC1®" and "Flutec PC3®" by the company BNFL Fluorochemicals; perfluoro-1,2-dimethylcyclobutane; perfluoroalkanes such as dodecafluoropentane and tetradecafluorohexane, sold under the names "PF 5050®" and "PF 5060®" by the company 3M, or alternatively bromoperfluorooctyl sold under the name "Foralkyl®" by the company Atochem; nonafluoromethoxybutane sold under the name "MSX4518®" by the company 3M and nonafluoroethoxyisobutane; perfluoromorpholine derivatives, such as the 4-trifluoromethylperfluoromorpholine sold under the name "PF 5052®" by the company 3M;

silicone oils, for instance volatile or non-volatile polymethylsiloxanes (PDMSs) containing a linear or cyclic silicone chain, that are liquid or pasty at room temperature, especially cyclopolydimethylsiloxanes (cyclomethicones) such as cyclohexasiloxane; polydimethylsiloxanes comprising alkyl, alkoxy or phenyl groups, that are pendent or at the end of a silicone chain, these groups containing from 2 to 24 carbon atoms; phenylsilicones, for instance phenyltrimethicones, phenyldimethicones, phenyltrimethylsiloxydiphenylsiloxanes, diphenyldimethicones, diphenylmethyldiphenyltrisiloxanes, 2-phenylethyltrimethyl-siloxysilicates and polymethylphenylsiloxanes;

mixtures thereof.

In the list of oils mentioned above, the expression "hydrocarbon-based oil" means any oil mainly comprising carbon and hydrogen atoms, and optionally ester, ether, fluoro, carboxylic acid and/or alcohol groups.

The other fatty substances that may be present in the oily phase are, for example, fatty acids containing from 8 to 30 carbon atoms, for instance stearic acid, lauric acid, palmitic acid and oleic acid; waxes, for instance lanolin, beeswax, carnauba wax or candelilla wax, paraffin waxes, lignite wax or microcrystalline waxes, ceresin or ozokerite, synthetic waxes such as polyethylene waxes, Fischer-Tropsch waxes; gums such as silicone gums (dimethiconol); silicone resins such as trifluoromethyl-C1–4-alkyldimethicone and trifluoro-propyldimethicone; and silicone elastomers, for instance the products sold under the names "KSG" by the company Shin-Etsu, under the names "Trefil", "BY29" or "EPSX" by the company Dow Corning or under the names "Gransil" by the company Grant Industries.

These fatty substances may be chosen in a varied manner by a person skilled in the art so as to prepare a composition having the desired properties, for example in terms of consistency or texture.

The emulsions may contain at least one emulsifier chosen from amphoteric, anionic, cationic and nonionic emulsifiers, used alone or as a mixture.

The emulsifiers are chosen in an appropriate manner depending on the emulsion to be obtained: water-in-oil (W/O) or oil-in-water (O/W) emulsions.

For the oil-in-water (O/W) emulsions, mention may be made, for example, of the following emulsifiers:

as amphoteric emulsifiers, N-acylamino acids such as N-alkylaminoacetates and disodium cocoamphodiacetate and amine oxides such as stearamine oxide;

as anionic emulsifiers, acylglutamates such as "disodium hydrogenated tallow glutamate" (Amisoft HS-21® sold by the company Ajinomoto); carboxylic acids and salts thereof such as sodium stearate; phosphoric esters and salts thereof such as "DEA oleth-10 phosphate"; sulphosuccinates such as "Disodium PEG-5 citrate lauryl sulphosuccinate" and "Disodium ricinoleamido MEA sulphosuccinate";

as cationic emulsifiers, alkyl-imidazolidiniums such as isostearyl-ethylimidonium ethosulphate; ammonium salts such as N,N,N-trimethyl-1-docosanaminium chloride (Behentrimonium chloride);

as nonionic emulsifiers, saccharide esters and ethers such as sucrose stearate, sucrose cocoate and the mixture of sorbitan stearate and of sucrose cocoate sold by the company ICI under the name Arlatone 2121®; polyol esters, in particular glycerol or sorbitol esters, such as glyceryl stearate, polyglyceryl-2 stearate and sorbitan stearate; glycerol ethers; oxyethylenated and/or oxypropylenated ethers such as the oxyethylenated, oxypropylenated ether of lauryl alcohol containing 25 oxyethylene groups and 25 oxypropylene groups (CTFA name "PPG-25 laureth-25") and the oxyethylenated ether of the mixture of $C_{12}$–$C_{15}$ fatty alcohols containing 7 oxyethylene groups (CTFA name "$C_{12}$–$C_{15}$ Pareth-7"); ethylene glycol polymers such as PEG-100.

For the water-in-oil (W/O) emulsions, mention may be made, for example, as emulsifiers, of fatty esters of a polyol, in particular of glycerol or of sorbitol, and in particular polyol isostearates, oleates and ricinoleates, such as the mixture of petrolatum, of polyglyceryl-3 oleate and of glyceryl isostearate, hydrogenated castor oil and of ozokerite, sold under the name Protegin W® by the company Goldschmidt, sorbitan isostearate, polyglyceryl diisostearate, polyglyceryl-2 sesquiisostearate; saccharide esters and ethers such as "methyl glucose dioleate"; fatty acid salts such as magnesium lanolate; dimethicone copolyols and alkyldimethicone copolyols such as Laurylmethicone copolyol sold under the name Dow Corning 5200 Formulation Aid by the company Dow Corning and Cetyl dimethicone copolyol sold under the name Abil EM 90® by the company Goldschmidt.

The emulsifiers may be introduced in their native form or in the form of mixtures with other emulsifiers and/or with other compounds such as fatty alcohols or oils.

The composition of the invention can also contain conventional adjuvants such as water-soluble or liposoluble dyes, pigments, fragrances, preserving agents, sunscreens, sequestering agents (EDTA), liposoluble or water-soluble active agents, and pH adjusters (acids or bases). These adjuvants are used in the proportions that are usual in cosmetics, and, for example, from 0.01 to 20% by weight relative to the total weight of the composition. These adjuvants and the concentrations thereof must be such that they do not modify the desired property for the composition.

Examples that may be mentioned of active agents that may be used in the composition of the invention include moisturizers, for example protein hydrolysates and polyols such as glycerol, glycols, for instance polyethylene glycols, and sugar derivatives; natural extracts; procyannidol oligomers; vitamins, for instance vitamin A (retinol), vitamin C (ascorbic acid), vitamin E (tocopherol), vitamin B5 (panthenol) and vitamin B3 or PP (niacinamide); urea; caffeine; depigmenting agents such as kojic acid and caffeic acid; salicylic acid; α-hydroxy acids such as lactic acid and glycolic acid; retinoids such as carotenoids; hydrocortisone;

melatonin; extracts of algae, fungi, plants, yeasts or bacteria; hydrolysed, partially hydrolysed or unhydrolysed proteins, and enzymes; antibacterial active agents for treating greasy skin, for instance 2,4,4'-trichloro-2'-hydroxydiphenyl ether (or Triclosan) and 3,4,4'-trichlorocarbanilide (or Triclocarban); fibres; and mixtures thereof.

The active agent(s) may be present, for example, in a concentration generally ranging from 0.01 to 20%, preferably from 0.1% to 10% and better still from 0.5% to 5% relative to the total weight of the composition.

The UV screening agents (or sunscreens) may be chosen from chemical screening agents, physical sunblock screening agents and mixtures of such screening agents. Examples of UV screening agents that may be mentioned include:

- butylmethoxydibenzoylmethane sold especially by the company Hoffmann-Laroche under the name Parsol 1789,
- octocrylene sold especially by the company BASF under the name Uvinul N539,
- octyl salicylate sold especially by the company Haarman-Reimer under the name Neo Heliopan OS,
- octyl methoxycinnamate sold especially by the company Hoffmann-Laroche under the name Parsol MCX,
- phenylbenzimidazolesulphonic acid sold especially by the company Merck under the name Eusolex 232,
- oxybenzones such as benzophenones-3, -4 or -5,
- benzotriazole silicones and in particular drometrizole trisiloxane,
- terephthalylidenedicamphorsulphonic acid, and
- titanium oxide or zinc oxide, in the form of microparticles or nanoparticles (nanopigments), that are optionally coated.

The composition of the invention may also contain fillers so as to modify the texture of the composition. As fillers that may be used in the composition of the invention, mention may be made, for example, besides pigments, of silica powder; talc; polyamide particles and especially those sold under the name Orgasol by the company Atochem; polyethylene powders;

microspheres based on acrylic copolymers, such as those based on ethylene glycol dimethacrylate/lauryl methacrylate copolymer sold by the company Dow Corning under the name Polytrap; expanded powders such as hollow microspheres and especially the microspheres sold under the name Expancel by the company Kemanord Plast or under the name Micropearl F 80 ED by the company Matsumoto; powders of natural organic materials such as crosslinked or noncrosslinked corn starch, wheat starch or rice starch, such as the powders of starch crosslinked with octenyl succinic anhydride, sold under the name Dry-Flo by the company National Starch; silicone resin microbeads such as those sold under the name Tospearl by the company Toshiba Silicone; and mixtures thereof. These fillers may be present in amounts ranging from 0% to 40% by weight and preferably from 1% to 10% by weight relative to the total weight of the composition.

The said composition thus finds a particular application as a cosmetic composition, which may be applied to keratin materials (the skin, the nails, the hair, the eyelashes, the eyebrows, mucous membranes and semi-mucous membranes, and any other area of body or facial skin).

The composition according to the invention contains a physiologically acceptable medium and finds its application in a large number of treatments, especially cosmetic treatments of keratin materials, in particular for the care (for example anti-ageing care), cleansing (and makeup removal), making up and/or antisun protection of keratin materials.

Thus, a subject of the present invention is the cosmetic use of the composition as defined above, for the care and/or cleansing and/or making up and/or antisun protection of keratin materials.

A subject of the invention is also a cosmetic treatment process for the care and/or cleansing and/or making up and/or antisun protection of keratin materials, which consists in applying to the keratin materials a composition as defined above.

The invention will now be described with reference to the following examples, relating to the preparation of macromonomers forming part of the composition of the polymers of the invention, to the preparation of polymers of the invention and to cosmetic compositions comprising the polymers of the invention.

EXAMPLES

Example 1
Synthesis of Macromonomers with an LCST

Example 1.1
Synthesis of a Macromonomer with an LCST Bearing Chains of a Random Copolymer of Oxypropylene and of Oxyethylene (Jeffamine® M-2005).

100 grams of Jeffamine® M-2005 (Huntsman), 4.3 grams of acrylic acid and 2.6 grams of potassium carbonate are introduced into a 500 ml reactor. The reaction medium is stirred at reflux for 2 hours. The hydrochloric acid formed is removed under vacuum. The macromonomer obtained consists of a random oligomer of polyoxypropylene (39 mol) and of poloxyethylene (6 mol) bearing a methylacrylamide function at one of its ends.

Example 1.2
Synthesis of a Difunctional Macromonomer with an LCST, Bearing Polyoxypropylene Chains (Jeffamine® D-2000).

100 grams of Jeffamine® D-2000 (Huntsman), 5.2 grams of methacrylic acid and 2.6 grams of potassium carbonate are introduced into a 500 ml reactor. The reaction medium is stirred for 2 hours at reflux. The hydrochloric acid formed is removed under vacuum. The macromonomer obtained consists of a polyoxypropylene oligomer bearing a methylacrylamide function at its two ends.

Example 1.2
Synthesis of a Macromonomer Bearing poly-N-isopropylacrylamide Chains This synthesis comprises two steps:

Synthesis of pNIPAM oligomers bearing an amino reactive end.

80 grams of N-isopropylacrylamide and 800 ml of osmosed water are introduced into a 2 500 ml three-necked round-bottomed flask equipped with a condenser and a nitrogen inlet. This mixture is heated, with stirring, to 29° C. using a water bath and nitrogen is bubbled through. After 45 minutes, 1.61 grams of aminoethanethiol hydrochloride pre-dissolved in 40 ml of osmosed water are added to the reaction medium. 5 minutes later, 1.91 grams of potassium persulphate dissolved in 80 ml of osmosed water are added to the reaction medium. This reaction medium is stirred under a nitrogen atmosphere for 3 hours at 29° C.

The monoamino poly-N-isopropylacrylamide (pNIPAM) oligomers thus synthesized are isolated by heating the reaction medium to 45° C. and filtration.

Synthesis of a pNIPAM macromonomer bearing an acrylamide end.

80 grams of pNIPAM oligomers bearing an amino end, 1.1 grams of methacrylic acid and 0.6 gram of potassium carbonate are introduced into a 500 ml reactor. The reaction medium is stirred at reflux for 2 hours. The hydrochloric acid formed is removed under vacuum. The macromonomer obtained consists of a pNIPAM oligomer bearing a methylacrylamide function at one of its ends.

Example 2

Copolymerization of Monomer(s) Containing an Unsaturated Hydrocarbon-Based Bond and of a Macromonomer with an LCST.

300 grams of tert-butanol are introduced into a 2 liter reactor equipped with a stirrer, a condenser, a thermometer, a thermostatically regulated bath, an addition funnel for introducing reagents and a gas inlet so as to control the atmosphere above the reaction medium. The reaction medium is placed under a nitrogen atmosphere, after bubbling nitrogen through for 30 minutes. X grams of acrylamido-2-methylpropanesulphonic acid (AMPS) are introduced with stirring and under a stream of nitrogen; the pH of the reaction medium is then equal to 1. Ammonia gas is introduced above the reaction medium until its pH is between 7 and 8. If necessary, $Y_i$ grams of the other comonomers i comprising at least one unsaturated function and Z grams of macromonomer(s) with an LCST, prepared in Example 1, are introduced into the reaction medium, which is then stirred for 1 hour; the pH is measured continuously so as to check that its value is between 7 and 8. The atmosphere above the reaction medium is again saturated with nitrogen so as to reduce the oxygen content in the liquid phase to a value of less than 1 ppm. 1 gram of azobisisobutyronitrile (AIBN) is introduced into the reaction medium under nitrogen and the temperature is adjusted to 60° C. As soon as the temperature reaches 60° C., the polymerization reaction starts. After about 30 minutes, the temperature is adjusted to the boiling point of the tert-butanol; the reaction medium is then refluxed with stirring for 2 hours.

The reaction medium then becomes a viscous suspension of polymer in the tert-butanol; the polymer is recovered by simple filtration of the tert-butanol, followed by drying under vacuum.

This procedure is used to synthesize the following water-soluble polymers, comprising monomer units of type (Ia) and/or (Ib) and macromonomers (II) with an LCST.

Example 2.1

| Reagents and solvent | Mass (g) |
| --- | --- |
| tert-Butanol | 300 |
| AMPS in ammonium salt form | 84 |
| Macromonomer derived from Jeffamine ® M-2005 | 36 |
| AIBN | 1 |

The copolymer obtained is composed of 70% by mass of AMPS (ammonium salt) and 30% of Jeffamine® M-2005 macromonomer; this corresponds to a molar content of 3.7% macromonomer in the copolymer. This polymer is non-crosslinked.

Example 2.2

| Reagents and solvent | Mass (g) |
| --- | --- |
| tert-Butanol | 300 |
| AMPS in ammonium salt form | 60 |
| Macromonomer derived from Jeffamine ® M-2005 | 60 |
| AIBN | 1 |

The copolymer obtained is composed of 50% by mass of AMPS (ammonium salt) and 50% of Jeffamine® M-2005 macromonomer; this corresponds to a molar content of 8.2% macromonomer in the copolymer. This polymer is non-crosslinked.

Example 2.3

| Reagents and solvent | Mass (g) |
| --- | --- |
| tert-Butanol | 300 |
| AMPS in ammonium salt form | 51 |
| N-Vinylacetamide | 21 |
| Macromonomer derived from Jeffamine ® M-2005 | 48 |
| AIBN | 1 |
| TMPTA | 1.51 |

The copolymer obtained is composed of 42% by mass of AMPS (ammonium salt), 17.3% N-vinylacetamide, 39.5% Jeffamine® M-2005 macromonomer and 1.2% TMPTA; this corresponds to a molar content of 3.8% macromonomer in the copolymer. This copolymer is crosslinked and the molar degree of crosslinking is equal to 1%.

Example 2.4

| Reagents and solvent | Mass (g) |
| --- | --- |
| tert-Butanol | 300 |
| AMPS in ammonium salt form | 84 |
| Macromonomer derived from Jeffamine ® M-2005 | 36 |
| Macromonomer derived from Jeffamine ® D-2000 | 3.9 |
| AIBN | 1 |

The copolymer obtained is composed of 67.8% by mass of AMPS (ammonium salt) and 29% Jeffamine® M-2005 macromonomer; this corresponds to a molar content of macromonomers with an LCST equal to 3.7%. This polymer is crosslinked with the difunctional macromonomer derived from Jeffamine® D-2000 and the molar degree of crosslinking is equal to 0.5%.

Example 2.5

| Reagents and solvent | Mass (g) |
| --- | --- |
| tert-Butanol | 300 |
| AMPS in ammonium salt form | 60 |
| Macromonomer derived from pNIPAM | 60 |
| AIBN | 1 |

The copolymer obtained is composed of 50% by mass of AMPS (ammonium salt) and 50% of pNIPAM macromonomer; this corresponds to a molar content of 2.2% macromonomer with an LCST in the copolymer. This polymer is not crosslinked.

Example 3
Heat-Induced Gelling Power of the Polymers Synthesized.

The heat-induced gelling power of the above copolymers was demonstrated by means of rheological measurements (Haake RS 150 rheometer, 35 mm/2° cone/plate), using 1% solutions of polymer in water, subjected to a shear rate of $10s^{-1}$. These measurements make it possible to determine the temperature above which the viscosity increases by heating, known as the gel point (Tgel).

| Polymer | Tgel (° C.) |
|---|---|
| Example 2.1 | 32 |
| Example 2.2 | 27 |
| Example 2.3 | 29 |
| Example 2.4 | 33 |
| Example 2.5 | 34 |

All the heat-induced gelling polymers obtained have a gel point in water, at a concentration of 1%, of less than 45° C., unlike the polymers described in patent EP 1 069 142.

Examples of cosmetic compositions comprising the polymer of the invention are given in the examples below.

Example 4
Body Milk
Composition

| | |
|---|---|
| Aqueous phase: | |
| Polymer of Example 2.2: | 0.4 g |
| Preserving agent | 0.2 g |
| Demineralized water | 84.4 g |
| Oily phase: | |
| Parleam oil | 9 g |
| Cyclohexadimethylsiloxane | 6 g |

The aqueous phase is prepared by dissolving the polymer of Example 2.2 in demineralized water containing the preserving agent, with stirring for 2 hours. The oily phase is then introduced slowly into the aqueous phase with stirring using a Moritz mixer at a speed of 4 000 rpm for 20 minutes.

The polymer of Example 2.2 makes it possible by itself to emulsify all of the oil phase. The formula obtained is an attractive fluid emulsion that can be used as a body milk.

Example 5
Fluid Foaming Composition.
Composition

| | |
|---|---|
| Polymer of Example 2.5: | 0.4 g |
| Glycerol | 5 g |
| Preserving agent | 0.4 g |
| Demineralized water | 94.2 g |

This foaming composition is obtained after dissolving the polymer of Example 2.5 in powder form in demineralized water with stirring at 25° C. for 2 hours; the other constituents are then introduced into this solution, which is stirred for 30 minutes.

The formulation obtained is a fluid foaming composition that may be used between 5° C. and 50° C. The polymer of Example 2.5 makes it possibly itself to obtain a foaming power.

French patent application 0106450 filed May 16, 2001 is incorporated herein by reference, as are all documents, references, texts, standards, patents and applications referred to above and immediately below.

The following references are noted:

[1] D. Hourdet et al., Polymer, 1994, Vol. 35, No. 12, pages 2624–2630.

[2] F. L'Alloret et al., Coll. Polym. Sci., 1995, Vol. 273, No. 12, pages 1163–1173.

[3] F. L'Alloret, Revue de l'Institut Français du Pétrole [Review of the French Petroleum Institute], 1997, Vol. 52, No. 2, pages 117–128.

[4] EP-A-0 583 814.

[5] EP-A-0 629 649.

[6] WO-A-95 24430.

[7] U.S. Pat. No. 5,939,485.

[8] WO-A-97 00275.

[9] WO-A-98 48768.

[10] WO-A-00 35961.

[11] Articles by Taylor et al., Journal of Polymer Science, part A: Polymer Chemistry, 1975,13,2551.

[12] J. Bailey et al., Journal of Applied Polymer Science, 1959, 1, 56.

[13] Heskins et al., Journal of Macromolecular Science, Chemistry A2, 1968, 1441.

[14] D. Hourdet et al., Polymer, 1997, Vol. 38, No. 10, pages 2535–2547.

[15] EP-A-1 069 142.

What is claimed is:

1. A water-soluble polymer comprising a water-soluble backbone and side units having in water a lower critical solution temperature, LCST, the polymer being obtainable by free-radical precipitation polymerization of:
   a) one or more water-soluble monomers (Ia) and, optionally, of one or more hydrophobic monomers (Ib) in a smaller amount relative to the monomer(s) (Ia), the monomers (Ia) and (Ib) bearing at least one unsaturated function that can be polymerized to form the water-soluble backbone;
   b) one or more macromonomers corresponding to formula (II):

$$A—X—B \qquad (II),$$

in which A is a group comprising at least one unsaturated hydrocarbon-based bond that may be polymerized; X is a group chosen from —O—, —S—, —PH—, —NH— and NR° in which R° is an alkyl group of 1 to 6 carbon atoms; and B is a unit with an LCST whose heat-induced demixing temperature in aqueous solution is from 5 to 40° C. for a concentration by weight in water of 1% of said unit.

2. The polymer according to claim 1, in which the heat-induced demixing temperature in aqueous solution of the units with an LCST of the polymer is from 10 to 35° C. for a concentration by weight in water of 1% of the said units.

3. The polymer according to claim 1, in which the water-soluble monomer(s) (Ia) is(are) selected from the following group of monomers, or salts thereof:

(meth)acrylic acid;
acrylamido-2-methylpropanesulphonic acid (AMPS);
styrenesulphonic acid;
vinylsulphonic acid;
(meth)allylsulphonic acid;
(meth)acrylamide;
vinylphosphonic acid;
N-vinylacetamide;
N-methyl-N-vinylacetamide;
N-vinylformamide;
N-methyl-N-vinylformamide;
N-vinyllactams comprising a cyclic alkyl group of 4 to 9 carbon atoms;
maleic anhydride;
itaconic acid;
vinyl alcohol of formula $CH_2=CHOH$;
dimethyldiallylammonium chloride;
quaternized dimethylaminoethyl methacrylate (DMAEMA);
(meth)acrylamidopropyltrimethylammonium chloride (APTAC and MAPTAC);
methylvinylimidazolium chloride;
2-vinylpyridine;
4-vinylpyridine;
glycidyl (meth)acrylate; and
vinyl monomers of formula (III) below:

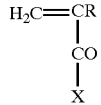
(III)

in which:
R is chosen from H, —$CH_3$, —$C_2H_5$ or —$C_3H_7$, and
X is chosen from:
alkyl oxides —OR' in which R' is a linear or branched, saturated or unsaturated hydrocarbon-based radical containing from 1 to 6 carbon atoms, optionally substituted with at least one halogen atom (iodine, bromine, chlorine or fluorine); a sulphonic (—$SO_3^-$), sulphate (—$SO_4^-$), phosphate (—$PO_4H_2$); hydroxyl (—OH); primary amine (—$NH_2$); secondary amine (—$NHR_1$), tertiary amine (—$NR_1R_2$) or quaternary amine (—$N^+R_1R_2R_3$) group with $R_1$, $R_2$ and $R_3$ being, independently of each other, a linear or branched, saturated or unsaturated hydrocarbon-based radical containing 1 to 6 carbon atoms, with the proviso that the sum of the carbon atoms of $R'+R_1+R_2+R_3$ does not exceed 6; and
—$NH_2$, —$NHR_4$ and —$NR_4R_5$ groups in which $R_4$ and $R_5$ are, independently of each other, linear or branched, saturated or unsaturated hydrocarbon-based radicals containing 1 to 6 carbon atoms, with the proviso that the total number of carbon atoms of $R_4+R_5$ does not exceed 6, $R_4$ and $R_5$ optionally being substituted with a halogen atom (iodine, bromine, chlorine or fluorine); a hydroxyl (—OH); sulphonic (—$SO_3^-$); sulphate (—$SO_4^-$); phosphate (—$PO_4H_2$); primary amine (—$NH_2$); secondary amine (—$NHR_1$), tertiary amine (—$NR_1R_2$) and/or quaternary amine (—$N^+R_1R_2R_3$) group with $R_1$, $R_2$ and $R_3$ being, independently of each other, a linear or branched, saturated or unsaturated hydrocarbon-based radical containing 1 to 6 carbon atoms, with the proviso that the sum of the carbon atoms of $R_4+R_5+R_1+R_2+R_3$ does not exceed 6.

4. A polymer according to claim 1, comprising hydrophobic monomer(s) (Ib) selected from the following group of monomers or salts thereof:
vinylacetate of formula $CH_2=CH-OCOCH_3$;
acrylonitrile;
vinyl chloride;
vinylidene chloride; and
vinyl monomers of formula (III) below:

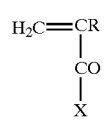
(III)

in which:
R is chosen from H, —$CH_3$, —$C_2H_5$ or —$C_3H_7$, and
X is chosen from:
alkyl oxides —OR' in which R' is a linear or branched, saturated or unsaturated hydrocarbon-based radical containing from 7 to 22 carbon atoms, optionally substituted with at least one halogen atom (iodine, bromine, chlorine or fluorine); a sulphonic (—$SO_3^-$), sulphate (—$SO_4^-$), phosphate (—$PO_4H_2$); hydroxyl (—OH); primary amine (—$NH_2$); secondary amine (—$NHR_1$), tertiary amine (—$NR_1R_2$) or quaternary amine (—$N^+R_1R_2R_3$) group with $R_1$, $R_2$ and $R_3$ being, independently of each other, a linear or branched, saturated or unsaturated hydrocarbon-based radical containing from 7 to 22 carbon atoms, with the proviso that the sum of the carbon atoms of $R'+R_1+R_2+R_3$ does not exceed 22; and
—$NH_2$, —$NHR_4$ and —$NR_4R_5$ groups in which $R_4$ and $R_5$ are, independently of each other, linear or branched, saturated or unsaturated hydrocarbon-based radicals containing 7 to 22 carbon atoms, with the proviso that the total number of carbon atoms of $R_4+R_5$ does not exceed 22, $R_4$ and $R_5$ optionally being substituted with a halogen atom (iodine, bromine, chlorine or fluorine); a hydroxyl (—OH); sulphonic (—$SO_3^-$); sulphate (—$SO_4^-$); phosphate (—$PO_4H_2$); primary amine (—$NH_2$); secondary amine (—$NHR_1$), tertiary amine (—$NR_1R_2$) and/or quaternary amine (—$N^+R_1R_2R_3$) group with $R_1$, $R_2$ and $R_3$ being, independently of each other, a linear or branched, saturated or unsaturated hydrocarbon-based radical containing 7 to 22 carbon atoms, with the proviso that the sum of the carbon atoms of $R_4+R_5+R_1+R_2+R_3$ does not exceed 22.

5. A polymer according to claim 4, in which the hydrophobic monomer(s) (Ib) is(are) present in an amount low enough for the water-soluble backbone of the polymer to be soluble in water.

6. A polymer according to claim 1, in which the water-soluble backbone is totally or partially neutralized with a mineral or organic base.

7. A polymer according to claim 6, in which the base is selected from the group consisting of sodium, ammonium, lithium, calcium and magnesium salts, salts of ammonium substituted with 1 to 4 alkyl groups containing from 1 to 15 carbon atoms, or alternatively from monoethanolamine, diethanolamine, triethanolamine, aminomethylpropanediol, N-methylglucamine and basic amino acids, and mixtures thereof.

8. A polymer according to claim 1, which is totally or partially crosslinked.

9. A polymer according to claim 8, which is totally or partially crosslinked with divinylbenzene, diallyl ether, triallylamine, tetraallylethylenediamine, dipropylene glycol diallyl ether, polyglycol diallyl ethers, hydroquinone diallyl ether, trimethylolpropane diallyl ether, tetraallyloxyethane, allylic ethers of alcohols of the sugar series, polyallyl esters, tetraallyloxyethanoyl or other polyfunctional alcohol allyl or vinyl ethers, triethylene glycol divinyl ether, allylic esters of vinylphosphonic acid and of phosphoric acid, compounds comprising two or three (meth)acrylate or (meth)acrylamide groups, and mixtures thereof.

10. A polymer according to claim 8, in which the crosslinking agent is allyl methacrylate, methylenebisacrylamide or trimethylolpropane triacrylate (TMPTA).

11. A polymer according to claim 8, in which the degree of crosslinking is from 0.01 mol % to 10 mol % relative to the polymer.

12. A polymer according to claim 8, which is totally or partially crosslinked by polymerizing, in addition to components a) and b), a multifunctional macromonomer containing units with an LCST.

13. A polymer according to claim 12, in which the multifunctional macromonomer with an LCST is polymerized in proportions making it possible to obtain a molar degree of crosslinking of from 0.01% to 10%.

14. A polymer according to claim 1, in which the water-soluble backbone has a molar mass of from 1 000 g/mol to 50 000 000 g/mol.

15. A polymer according to claim 1, in which the group A of the macromonomer(s) of formula (II) is selected from the group consisting of vinyl, allyl, acryl and methacryl groups.

16. A polymer according to claim 1, in which the units B with an LCST of the macromonomer of formula (II) consist of one or more polymers selected from the group of the following polymers:

polyethers, polyvinyl methyl ethers, polymeric and copolymeric N-substituted acrylamide derivatives with an LCST, and poly-N-vinylcaprolactam and N-vinylcaprolactam copolymers.

17. A polymer according to claim 1, in which the units with an LCST of the polymer consist of polypropylene oxide $(PPO)_n$ with n being an integer from 10 to 50, or of random copolymers of ethylene oxide (EO) and of propylene oxide (PO), represented by the formula $(EO)_m(PO)_n$ in which m is an integer ranging from 1 to 40, and n is an integer ranging from 10 to 60.

18. A polymer according to claim 17, in which the molar weight of the units with an LCST of the polymer is from 500 to 5 300 g/mol.

19. A polymer according to claim 1, in which the units with an LCST of the polymer consist of a polymer chosen from poly-N-isopropylacrylamide, poly-N-ethylacrylamide and copolymers of N-isopropylacrylamide or of N-ethylacrylamide and of one or more monomer(s) chosen from the the following list:

(meth)acrylic acid;

acrylamido-2-methylpropanesulphonic acid (AMPS);

styrenesulphonic acid;

vinylsulphonic acid;

(meth)allylsulphonic acid;

(meth)acrylamide;

vinylphosphonic acid;

N-vinylacetamide;

N-methyl-N-vinylacetamide;

N-vinylformamide;

N-methyl-N-vinylformamide;

N-vinyllactams comprising a cyclic alkyl group of 4 to 9 carbon atoms;

maleic anhydride;

itaconic acid;

vinyl alcohol of formula $CH_2=CHOH$;

dimethyldiallylammonium chloride;

quaternized dimethylaminoethyl methacrylate (DMAEMA);

(meth)acrylamidopropyltrimethylammonium chloride (APTAC and MAPTAC);

methylvinylimidazolium chloride;

2-vinylpyridine;

4-vinylpyridine;

glycidyl (meth)acrylate; and vinyl monomers of formula (III) below:

in which:

R is chosen from H, —$CH_3$, —$C_2H_5$ or —$C_3H_7$, and

X is chosen from:

alkyl oxides —OR' in which R' is a linear or branched, saturated or unsaturated hydrocarbon-based radical containing from 1 to 6 carbon atoms, optionally substituted with at least one halogen atom (iodine, bromine, chlorine or fluorine); a sulphonic (—$SO_3^-$), sulphate (—$SO_4^-$), phosphate (—$PO_4H_2$); hydroxyl (—OH); primary amine (—$NH_2$); secondary amine (—$NHR_1$), tertiary amine (—$NR_1R_2$) or quaternary amine (—$N^+R_1R_2R_3$) group with $R_1$, $R_2$ and $R_3$ being, independently of each other, a linear or branched, saturated or unsaturated hydrocarbon-based radical containing 1 to 6 carbon atoms, with the proviso that the sum of the carbon atoms of $R'+R_1+R_2+R_3$ does not exceed 6; and —$NH_2$, —$NHR_4$ and —$NR_4R_5$ groups in which $R_4$ and $R_5$ are, independently of each other, linear or branched, saturated or unsaturated hydrocarbon-based radicals containing 1 to 6 carbon atoms, with the proviso that the total number of carbon atoms of $R_4+R_5$ does not exceed 6, $R_4$ and $R_5$ optionally being substituted with a halogen atom (iodine, bromine, chlorine or fluorine); a hydroxyl (—OH); sulphonic (—$SO_3^-$); sulphate (—$SO_4^-$); phosphate (—$PO_4H_2$); primary amine (—NH2); secondary amine (—$NHR_1$), tertiary amine (—$NR_1R_2$) and/or quaternary amine (—$N^+$ $R_1R_2R_3$) group with $R_1$, $R_2$ and $R_3$ being, independently of each other, a linear or branched, saturated or unsaturated hydrocarbon-based radical containing 1 to 6 carbon atoms, with the proviso that the sum of the carbon atoms of $R_4+R_5+R_1+R_2+R_3$ does not exceed 6;

vinylacetate of formula $CH_2=CH—OCOCH_3$;
acrylonitrile;
vinyl chloride;
vinylidene chloride; and
vinyl monomers of formula (III) below:

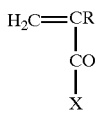

(III)

in which:
R is chosen from H, —$CH_3$, —$C_2H_5$ or -$C_3H_7$, and
X is chosen from:
alkyl oxides —OR' in which R' is a linear or branched, saturated or unsaturated hydrocarbon-based radical containing from 7 to 22 carbon atoms, optionally substituted with at least one halogen atom (iodine, bromine, chlorine or fluorine); a sulphonic (—$SO_3^-$), sulphate (—$SO_4^-$), phosphate (—$PO_4H_2$); hydroxyl (—OH); primary amine (—$NH_2$); secondary amine (—$NHR_1$), tertiary amine (—$NR_1R_2$) or quaternary amine (—$N^+R_1R_2R_3$) group with $R_1$, $R_2$ and $R_3$ being, independently of each other, a linear or branched, saturated or unsaturated hydrocarbon-based radical containing from 7 to 22 carbon atoms, with the proviso that the sum of the carbon atoms of $R'+R_1+R_2+R_3$ does not exceed 22; and
—$NH_2$, —$NHR_4$ and —$NR_4R_5$ groups in which $R_4$ and $R_5$ are, independently of each other, linear or branched, saturated or unsaturated hydrocarbon-based radicals containing 7 to 22 carbon atoms, with the proviso that the total number of carbon atoms of $R_4+R_5$ does not exceed 22, $R_4$ and $R_5$ optionally being substituted with a halogen atom (iodine, bromine, chlorine or fluorine); a hydroxyl (—OH); sulphonic (—$SO_3^-$); sulphate (—$SO_4^-$); phosphate (—$PO_4H_2$); primary amine (—$NH_2$); secondary amine (—$NHR_1$), tertiary amine (—$NR_1R_2$) and/or quaternary amine (—$N^+R_1R_2R_3$) group with $R_1$, $R_2$ and $R_3$ being, independently of each other, a linear or branched, saturated or unsaturated hydrocarbon-based radical containing 7 to 22 carbon atoms, with the proviso that the sum of the carbon atoms of $R_4+R_5+R_1+R_2+R_3$ does not exceed 22.

20. A polymer according to claim 19, in which the molar weight of the units with an LCST of the polymer is from 1000 g/mol to 30,000 g/mol.

21. A polymer according to claim 1, in which the units with an LCST of the polymer consist of a poly-N-vinylcaprolactam or a copolymer of N-vinylcaprolactam and of one or more monomer(s) chosen from the following list:
(meth)acrylic acid;
acrylamido-2-methylpropanesulphonic acid (AMPS);
styrenesulphonic acid;
vinylsulphonic acid;
(meth)allylsulphonic acid;
(meth)acrylamide;
vinylphosphonic acid;
N-vinylacetamide;
N-methyl-N-vinylacetamide;
N-vinylformamide;
N-methyl-N-vinylformamide;
N-vinyllactams comprising a cyclic alkyl group of 4 to 9 carbon atoms;
maleic anhydride;
itaconic acid;
vinyl alcohol of formula $CH_2=CHOH$;
dimethyldiallylammonium chloride;
quaternized dimethylaminoethyl methacrylate (DMAEMA);
(meth)acrylamidopropyltrimethylammonium chloride (APTAC and MAPTAC);
methylvinylimidazolium chloride;
2-vinylpyridine;
4-vinylpyridine;
glycidyl (meth)acrylate; and
vinyl monomers of formula (III) below:

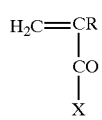

(III)

in which:
R is chosen from H, —$CH_3$, —$C_2H_5$ or —$C_3H_7$, and
X is chosen from:
alkyl oxides —OR' in which R' is a linear or branched, saturated or unsaturated hydrocarbon-based radical containing from 1 to 6 carbon atoms, optionally substituted with at least one halogen atom (iodine, bromine, chlorine or fluorine); a sulphonic (—$SO_3^-$) sulphate (—$SO_4^-$), phosphate (—$PO_4H_2$); hydroxyl (—OH); primary amine (—$NH_2$); secondary amine (—$NHR_1$), tertiary amine (—$NR_1R_2$) or quaternary amine (—$N^+R_1R_2R_3$) group with $R_1$, $R_2$ and $R_3$ being, independently of each other, a linear or branched, saturated or unsaturated hydrocarbon-based radical containing 1 to 6 carbon atoms, with the proviso that the sum of the carbon atoms of $R'+R_1+R_2+R_3$ does not exceed 6; and
—$NH_2$, —$NHR_4$ and —$NR_4R_5$ groups in which R and $R_5$ are, independently of each other, linear or branched, saturated or unsaturated hydrocarbon-based radicals containing 1 to 6 carbon atoms, with the proviso that the total number of carbon atoms of $R_4+R_5$ does not exceed 6, $R_4$ and $R_5$ optionally being substituted with a halogen atom (iodine, bromine, chlorine or fluorine); a hydroxyl (—OH); sulphonic (—$SO_3^-$); sulphate (—$SO_4^-$); phosphate (—$PO_4H_2$); primary amine (—$NH_2$); secondary amine (—$NHR_1$), tertiary amine (—$NR_1R_2$) and/or quaternary amine (—$N^+R_1R_2R_3$) group with $R_1$, $R_2$ and $R_3$ being, independently of each other, a linear or branched, saturated or unsaturated hydrocarbon-based radical containing 1 to 6 carbon atoms, with the proviso that the sum of the carbon atoms of $R_4+R_5+R_1+R_2+R_3$ does not exceed 6;

vinylacetate of formula $CH_2=CH—OCOCH_3$;

acrylonitrile;

vinyl chloride;

vinylidene chloride; and vinyl monomers of formula (III) below:

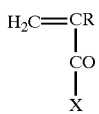 (III)

in which:

R is chosen from H, $—CH_3$, $—C_2H_5$ or $—C_3H_7$, and X is chosen from:

alkyl oxides $—OR'$ in which R' is a linear or branched, saturated or unsaturated hydrocarbon-based radical containing from 7 to 22 carbon atoms, optionally substituted with at least one halogen atom (iodine, bromine, chlorine or fluorine); a sulphonic ($—SO_3^-$), sulphate ($—SO_4^-$), phosphate ($—PO_4H_2$); hydroxyl ($—OH$); primary amine ($—NH_2$); secondary amine ($—NHR_1$), tertiary amine ($—NR_1R_2$) or quaternary amine ($—N^+R_1R_2R_3$) group with $R_1$, $R_2$ and $R_3$ being, independently of each other, a linear or branched, saturated or unsaturated hydrocarbon-based radical containing from 7 to 22 carbon atoms, with the proviso that the sum of the carbon atoms of $R'+R_1+R_2+R_3$ does not exceed 22; and $—NH_2$, $—NHR_4$ and $—NR_4R_5$ groups in which $R_4$ and $R_5$ are, independently of each other, linear or branched, saturated or unsaturated hydrocarbon-based radicals containing 7 to 22 carbon atoms, with the proviso that the total number of carbon atoms of $R_4+R_5$ does not exceed 22, $R_4$ and $R_5$ optionally being substituted with a halogen atom (iodine, bromine, chlorine or fluorine); a hydroxyl ($—OH$); sulphonic ($—SO_3^-$); sulphate ($—SO_4^-$); phosphate ($—PO_4H_2$); primary amine ($—NH_2$); secondary amine ($—NHR_1$), tertiary amine ($—NR_1R_2$) and/or quaternary amine ($—N^+R_1R_2R_3$) group with $R_1$, $R_2$ and $R_3$ being, independently of each other, a linear or branched, saturated or unsaturated hydrocarbon-based radical containing 7 to 22 carbon atoms, with the proviso that the sum of the carbon atoms of $R_4+R_5+R_1+R_2+R_3$ does not exceed 22.

22. A polymer according to claim 21, in which the molar weight of the units with an LCST is from 1 000 to 30 000 g/mol.

23. A polymer according to claim 1, in which the proportion by weight of the units with an LCST of the polymer is from 5% to 70% relative to the polymer.

24. A process for preparing the water-soluble polymer according to claim 1, comprising:

performing a free-radical precipitation copolymerization of one or more water-soluble monomers (Ia), optionally of one or more hydrophobic monomers (Ib), and of one or more macromonomers of formula (II) in a medium comprising an alcohol and water.

25. A process according to claim 24, in which the alcohol is an aliphatic alcohol containing from 1 to 4 carbon atoms.

26. A process according to claim 24, in which the medium has a water content of less than 10% by weight.

27. A process according to claim 24, in which the free-radical copolymerization is performed at a temperature of between −10C and 100° C.

28. A process according to claim 24, in which the copolymerization is performed in the presence of a copolymerization initiator that generates free radicals.

29. A process according to claim 28, in which the copolymerization initiator is selected from the group consisting of aqueous hydrogen peroxide solution; organic peroxidized compounds; diazo compounds; and oxidizing agent/reducing agent couples.

30. A process according to claim 24, in which the copolymerization is initiated with a photoinitiator.

31. A process according to claim 24, in which the copolymerization is initiated by radiation.

32. A process according to claim 24, in which the copolymerization is carried out in inert medium, optionally under a nitrogen or argon atmosphere.

33. An aqueous composition comprising at least one polymer as defined according to claim 1, and an aqueous phase.

34. The composition according to claim 33, in which the polymer is present in an amount of between 0.01% and 20% by weight.

35. The composition according to claim 33, further comprising a physiologically, cosmetically or dermatologically acceptable medium.

36. A process, comprising the cleansing and/or making up and/or caring for and/or protecting from sun of keratin material, wherein the composition of claim 33 is applied to keratin material.

37. The polymer of claim 2, in which the heat-induced demixing temperature is from 10 to 30° C.

38. The polymer of claim 17, wherein m is an integer of from 2 to 10.

39. The polymer of claim 18, in which the molar weight is from 1500 to 3000.

* * * * *

UNITED STATES PATENT AND TRADEMARK OFFICE
CERTIFICATE OF CORRECTION

PATENT NO.   : 6,689,856 B2
DATED        : February 10, 2004
INVENTOR(S)  : Florence L'Alloret It is certified that error appears in the above-identified patent and that said Letters Patent is hereby corrected as shown below:

Column 26,
Line 66, "(-NH2)" should read -- ($NH_2$) --.

Column 28,
Line 53, "R" (last occurrence) should read -- $R_4$ --.

Signed and Sealed this

First Day of June, 2004

JON W. DUDAS
*Acting Director of the United States Patent and Trademark Office*